United States Patent [19]

Nikkel

[11] Patent Number: 5,291,029

[45] Date of Patent: Mar. 1, 1994

[54] APPARATUS FOR MEASURING PAPER WEB PROPERTIES WHILE IN SITU OF THE PAPER MACHINE WITH AIR JET STABILIZATION

[75] Inventor: Willem A. Nikkel, Covington, Va.

[73] Assignee: Westvaco Corporation, New York, N.Y.

[21] Appl. No.: 59,961

[22] Filed: May 13, 1993

[51] Int. Cl.$^5$ .............................................. G01N 21/86
[52] U.S. Cl. ..................................... 250/571; 356/429
[58] Field of Search ............................... 250/571–572, 250/562, 563; 356/429–431, 433, 434

[56] References Cited

U.S. PATENT DOCUMENTS

| 4,288,160 | 9/1981 | Lodzinski | 356/429 |
| 4,319,847 | 3/1982 | Howarth | 250/571 |
| 5,159,189 | 10/1992 | Anderegg et al. | 356/429 |
| 5,166,536 | 11/1992 | Rye | 250/571 |

OTHER PUBLICATIONS

Troubleshooting with Wet-End Tuning, O. Kalmes and D. Murdock, Paper (London) 202, No. 6: 18; Oct. 22, 1984.
M/K Systems Inc. On-Line Formation Tester (no date).
Instruction Manual for the M/K Systems, Inc. Machine Mounted, On-Line Formation Tester, Model M/K620, S#F2014, Jul., 1989.

Primary Examiner—David C. Nelms
Attorney, Agent, or Firm—W. A. Marcontell; J. R. McDaniel; R. L. Schmalz

[57] ABSTRACT

An in situ traveling paper machine web is stabilized from flutter and vibration for the purpose of formation and optical property measurement by an air flow system by which a boundary layer air stream between a sole plate and the adjacent web surface secures the web in a stable position.

2 Claims, 2 Drawing Sheets

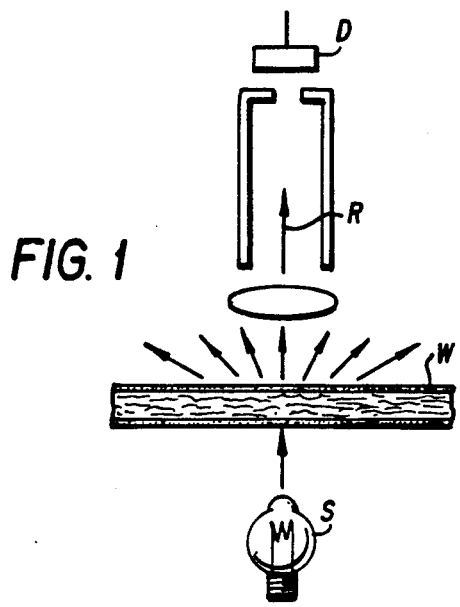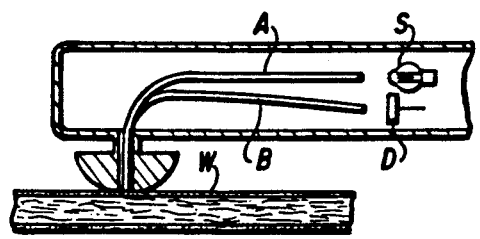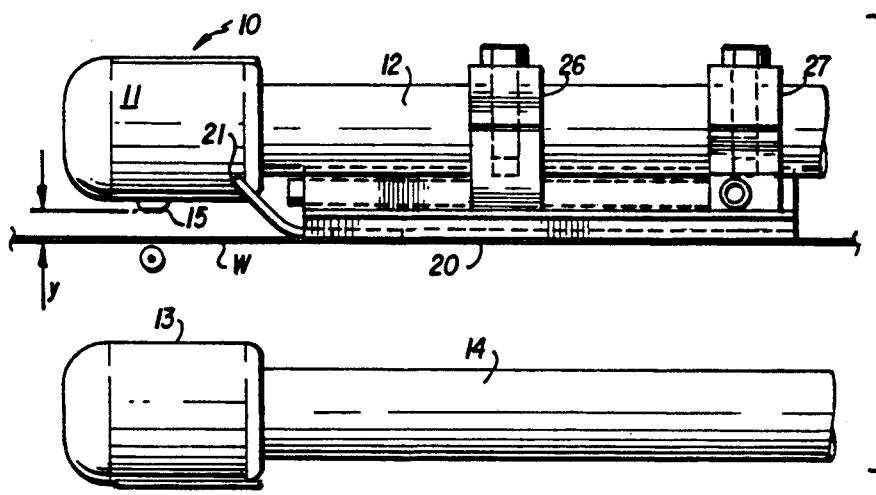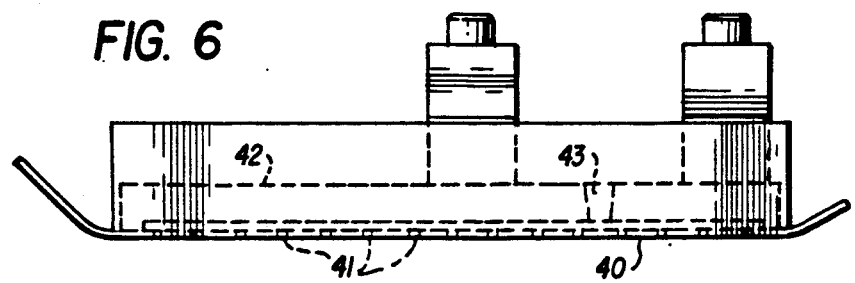

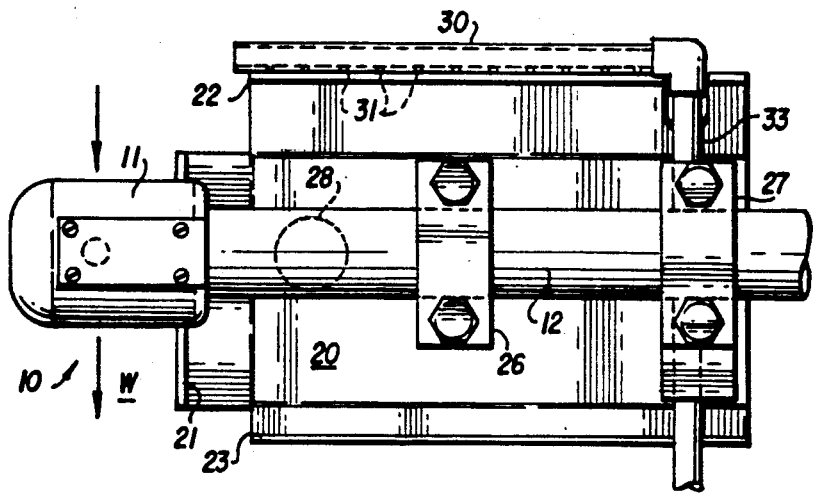
FIG. 4
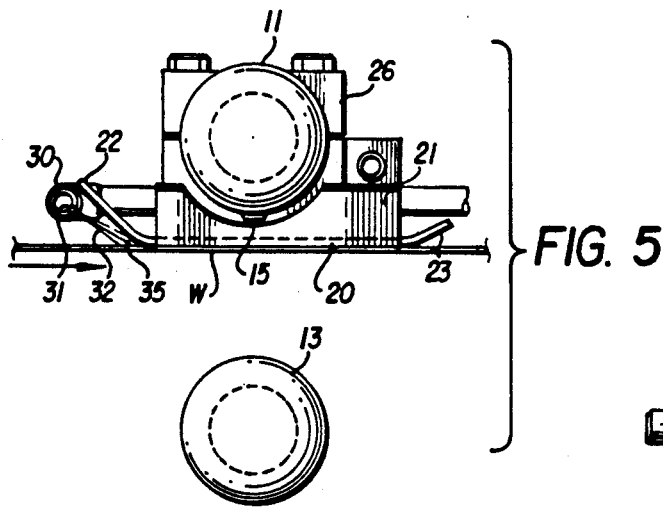
FIG. 5
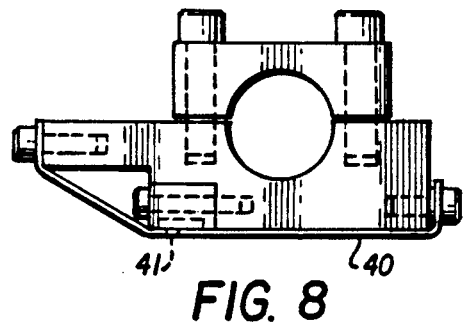
FIG. 8
FIG. 7
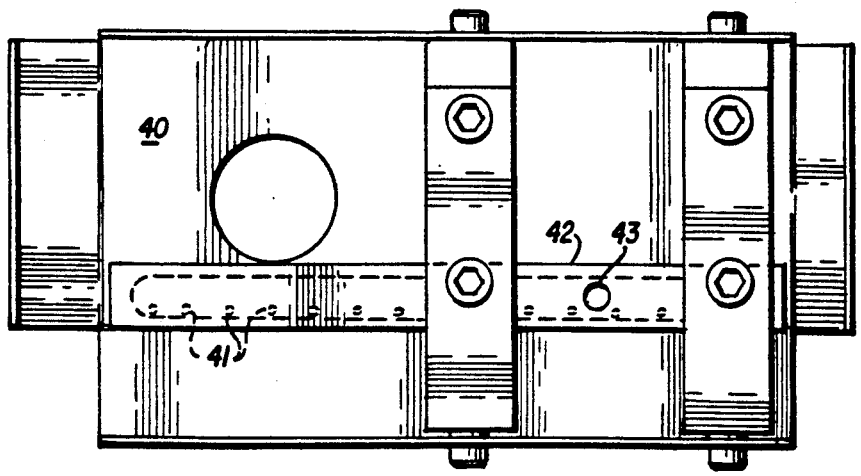

APPARATUS FOR MEASURING PAPER WEB PROPERTIES WHILE IN SITU OF THE PAPER MACHINE WITH AIR JET STABILIZATION

BACKGROUND OF THE INVENTION

1. Field of the Invention

The present invention relates to the art and science of papermaking. More particularly, the invention relates to a method and apparatus for measuring paper web properties while in situ of the paper machine.

2. Description of the Prior Art

Throughout the production of a fourdrinier machine paper web, certain quality and property characteristics of the web are continuously monitored and measured. Among such monitored properties are those relating to surface smoothness, optical uniformity and formation quality.

Paper web formation quality is that characteristic of paper that is manually ascertained by the uniformity of light transmittance through a back lighted web. A mottled sheet is of poor formation quality. The characteristic is objectively measured by detecting variations in light transmittance through a given length of web from a constant intensity source. Maintenance of a constant intensity light source requires a constant physical displacement position of the web from the light source within a fixed separation gap between the light source and light detector. At a web production velocity of 1500 feet per minute and greater, the web begins to flutter and float at unsupported locations along the machine length. Necessarily, detector heads of measuring instruments must be located at unsupported web locations.

As a general rule, no stationary structure is permitted to have contact with the traveling paper machine web. This practicer has numerous justifications including a potential for marking or scoring the web, as a machine threading obstruction and as a surface of debris accumulation and web contamination.

Resultantly, the accuracy and reliability of web property measuring instruments such as formation testers and monitors is greatly compromised on high speed paper machines due to a heretofore conflict between the measuring requirement to hold a constant web position proximity and the machine operating discipline that denies the presence of structure necessary to confine the web position.

It is, therefore, an object of the present invention to provide a method and apparatus for maintaining the proximity of an in situ paper machine web to a web property measuring unit.

Another object of the present invention is to provide a method and apparatus that secures a point position of an in situ paper machine web without structural contact.

Another object of the present invention is to improve the accuracy of formation monitors and other in situ web property measuring instruments by stabilizing the web location relative to the instrument measuring means.

SUMMARY OF THE INVENTION

These and other objects of the invention to subsequently become apparent are accomplished by provision of a sole plate structure between an instrument emitter and detector. An aperture is provided in the sole plate structure to accommodate passage of an energy beam from the emitter to the detector.

This sole plate is rigidly located adjacent the in situ web running position with a planar parallel orientation.

Adjacent an upstream end of the sole plate relative to the web running direction, an instrument air conduit is positioned to direct a small air jet between the web and sole plate. Fluid from this jet establishes a stable boundary layer between the web and sole plate.

Pressure differential respective to opposite web sides at the boundary layer region secures the web position relative to the sole plate without physical or structural contact therewith.

DESCRIPTION OF THE DRAWINGS

Relative to the drawings wherein like reference characters designate like or similar elements throughout the several figures of the drawings:

FIG. 1 is an operating principal schematic for a through-web light transmission instrument.

FIG. 2 is an operating principal schematic for surface reflected light stimulation instrument.

FIG. 3 is an elevational side view of the invention oriented parallel-planar with a cooperative paper machine web.

FIG. 4 is a plan view of the invention.

FIG. 5 is an end elevational view of the invention oriented parallel-planar with a cooperative paper machine web.

FIG. 6 is a side elevation of an alternative embodiment of the invention sole plate subassembly.

FIG. 7 is a plan view of the alternative embodiment invention sole plate subassembly.

FIG. 8 is an end elevation of the alternative embodiment invention sole plate subassembly.

DESCRIPTION OF THE PREFERRED EMBODIMENT

What is actually seen when a sheet of paper is viewed is light reflected or scattered from its unbonded internal surfaces; fibers, per se, are virtually transparent. In the case of transmission measurements as represented by FIG. 1, a known intensity of light is directed into a sheet W on one side thereof from a source S and the remaining value R emerging from the other side is measured by a photo detector D. The light value differential is scattered away from the direct line of sight between the emitter S and photo detector D. Therefore, the heavier the zone of light transmission through the sheet, the less light is transmitted. When the sheet caliper is substantially constant, variations in light transmissivity are due to localized regions of greater fiber density. Hence, formation variability.

In the case of reflected measurements, as represented by FIG. 2, the converse measurement applies. Fiber bundles A are used to transmit light from the source S to the web surface. Reflections from that surface are returned along fiber bundles B to the photo detector D. More light is reflected from heavier or denser web zones than from lighter ones because the former have, I more internal scattering surfaces.

In either case, whether by transmissive or reflective measuring mode, constancy of web proximity to the light source S is essential for measurement accuracy and reliability. However, physically contacting guide structure is impermissible. For this purpose, an air jet augmented sole plate unit is secured to an instrument mounting frame to positionally stabilize the web W at the critical point of light beam intersection.

In application to a transmissive instrument 10, the light source S is mounted within an emission head 11 held over an unsupported segment of an in situ paper machine web W by a cantilever tube 12 as shown by FIGS. 3, 4 and 5. A corresponding photo detector D is mounted within the reception head 13, also at the end of a cantilever tube 14. Commonly, both cantilever tubes are 12 to 24 inches long, measured from a paper machine frame mounting base not shown.

In a reflective instrument application, both emissive source S and detector D are housed in the same head unit 13. Consequently, no lower cantilever tube 14 would be required.

The sole plate unit of FIGS. 3, 4 and 5 comprises a base plate 20 having at least three of four rectangular edges curled as at 21, 22 and 23 for fairleading. Tube mounting brackets 26 and 27 secure the base plate 20 to the emitter tube 12. These mounting brackets 26 and 27 structurally position the controlled distance Y between the emitter head 11 collimator lens 15 and the web W.

The invention configuration of FIGS. 3, 4 and 5 illustrates the emitter and detector heads 11 and 13 projected beyond the base plate edge 21. Reference to the web traveling direction orientation arrows shows the heads 11 and 13 to be projected in the cross-machine direction from the structural limit of base plate edge 21. In this pattern, side edge 22 is the upstream (relative to the web W traveling direction) edge and edge 23 is the downstream edge.

Operational circumstances frequently arise that require the emitter and detector heads 11 and 13 to be located within the projected plan of the base plate edges. For this purpose, an aperture 28 is provided through the base plate 20 section.

Positioned upstream of the base plate edge 22 is an air distribution manifold 30 having a plurality of apertures 31 for discharging respective air jets 32. A supply conduit 33 secured to the mounting bracket 27 carries 5 to 30 psi regulated, dried and filtered instrument air to the distribution manifold. Air jets 32 are aimed at the in running nip 35 between the web W and the base plate 20. Boundary layer fluid dynamics will attach the web W to a stable standoff distance, usually in the order of 0.001 to 0.005 inch, from the proximate base plate surface.

FIGS. 6, 7 and 8 represent an alternative embodiment of the invention sole plate unit isolated from the instrument support tubes. In this embodiment, the air jet discharge apertures 41 penetrate the structure of base plate 40 to inject the boundary layer air film directly into the interface between the base plate and the web.

Structurally, these apertures 41 are supplied from a channel manifold block 42 having a fluid tight interface seal between the block face and the base plate top surface.

Instrument supply air is admitted to the block channel by a conduit port 43.

Having fully described the preferred embodiments of my invention, those of ordinary skill in the art will perceive equivalent applications. As my invention, however,

I claim:

1. An apparatus for stabilizing a position of a traveling paper web relative to a web formation monitoring means, said monitoring means have a photon emission means for transmitting a light beam through said traveling web, a sole plate means for establishing a reference plane at a predetermined displacement distance from said emission means and a boundary layer air jet means for directing a flow of air against said web in a zone between said web and said sole plate means to stabilize said web at a position of close, parallel proximity with said reference plane.

2. An apparatus for stabilizing a position of a traveling paper web relative to a web property monitoring means, said monitoring means having a photon emission means for directing a light beam against a surface of said traveling web, a sole plate means, having first and second ends for establishing a reference plane at a predetermined displacement distance from said emission means, a boundary layer air jet means, and a nip located adjacent to said air jet means and said first end of said sole plate means such that said air jet means directs a flow of air against said web substantially at said nip to stabilize said web at a position of close, parallel proximity with said reference plane.

* * * * *

UNITED STATES PATENT AND TRADEMARK OFFICE
CERTIFICATE OF CORRECTION

PATENT NO. : 5,291,029
DATED : March 1, 1994
INVENTOR(S) : Willem A. Nikkel

It is certified that error appears in the above-indentified patent and that said Letters Patent is hereby corrected as shown below:

Column 2, line 61, delete --,I--.

Signed and Sealed this

Twenty-eighth Day of June, 1994

Attest:

BRUCE LEHMAN

Attesting Officer     Commissioner of Patents and Trademarks